United States Patent
Vukos et al.

(10) Patent No.: US 6,702,800 B1
(45) Date of Patent: Mar. 9, 2004

(54) ABSORBENT GARMENT WITH TRANSVERSE AND LONGITUDINAL STRETCH

(75) Inventors: John Philip Vukos, Neenah, WI (US); Georgia Lynn Zehner, Larsen, WI (US); Duane Girard Uitenbroek, Little Chute, WI (US); Richard Warren Tanzer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 137 days.

(21) Appl. No.: 09/698,496

(22) Filed: Oct. 27, 2000

(51) Int. Cl.$^7$ ................................................ A61F 13/15
(52) U.S. Cl. ...................... 604/385.22; 604/385.01; 604/385.16; 604/385.28; 604/385.23; 604/385.24
(58) Field of Search ..................... 604/385.22, 385.16, 604/385.28, 385.23, 385.24, 385.01

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,340,563 A | 7/1982 | Appel et al. | |
| 4,443,513 A | 4/1984 | Meitner et al. | |
| 4,543,099 A | 9/1985 | Bunnelle et al. | |
| 4,606,964 A | 8/1986 | Wideman | |
| 4,640,726 A | 2/1987 | Sallee et al. | |
| 4,687,477 A | 8/1987 | Suzuki et al. | |
| 4,701,170 A | 10/1987 | Wilson et al. | |
| 4,701,171 A | 10/1987 | Boland et al. | |
| 4,701,176 A | 10/1987 | Wilson et al. | |
| 4,704,116 A | 11/1987 | Enloe | |
| 4,720,415 A | 1/1988 | Vander Wielen et al. | |
| 4,756,709 A | 7/1988 | Stevens | |
| 4,801,485 A | 1/1989 | Sallee et al. | |
| 4,820,572 A | 4/1989 | Killian et al. | |
| 4,834,736 A | 5/1989 | Boland et al. | |
| 4,863,779 A | 9/1989 | Daponte | |
| 4,895,569 A | 1/1990 | Wilson et al. | |
| 4,908,247 A | 3/1990 | Baird et al. | |
| 4,923,742 A | 5/1990 | Killian et al. | |
| 4,938,757 A | * 7/1990 | Van Gompel et al. | ...... 604/396 |
| 4,965,122 A | 10/1990 | Morman | |
| 4,981,747 A | 1/1991 | Morman | |
| 4,990,147 A | 2/1991 | Freeland | |
| 5,114,781 A | 5/1992 | Morman | |
| 5,143,679 A | 9/1992 | Weber et al. | |
| 5,156,793 A | 10/1992 | Buell et al. | |

(List continued on next page.)

FOREIGN PATENT DOCUMENTS

| | | |
|---|---|---|
| EP | 0 236 032 | 12/1991 |
| EP | 0 386 816 | 4/1994 |
| EP | 0 591 647 | 4/1994 |
| EP | 0 400 111 | 8/1994 |
| EP | 0 451 705 | 8/1994 |

(List continued on next page.)

Primary Examiner—Weilun Lo
Assistant Examiner—Jacqueline Stephens
(74) Attorney, Agent, or Firm—Pauley Petersen & Erickson

(57) ABSTRACT

A form-fitting, pant-like, absorbent garment that delivers an optimal amount and direction of stretch to provide optimal fit and comfort. The absorbent garment has an outer cover with a back panel, a crotch panel and a front panel. The back panel and the front panel can each stretch in a transverse direction, and the crotch panel can stretch in a longitudinal direction. Seams joining the front and back panels to the crotch panel provide non-stretch zones that may be positioned to control fit forces. The garment provides enhanced fit and comfort during use, and ease of application with a self-adjusting feature.

31 Claims, 3 Drawing Sheets

U.S. PATENT DOCUMENTS

| | | |
|---|---|---|
| 5,167,897 A | 12/1992 | Weber et al. |
| 5,171,388 A | 12/1992 | Hoffman et al. |
| 5,226,992 A | 7/1993 | Morman |
| 5,244,482 A | 9/1993 | Hassenboehler, Jr. et al. |
| 5,259,902 A | 11/1993 | Muckenfuhs |
| 5,269,775 A | 12/1993 | Freeland et al. |
| 5,336,545 A | 8/1994 | Morman |
| 5,354,400 A | 10/1994 | Lavash et al. |
| 5,385,775 A | 1/1995 | Wright |
| 5,397,316 A | 3/1995 | LaVon et al. |
| 5,492,753 A | 2/1996 | Levy et al. |
| 5,496,429 A | 3/1996 | Hasse et al. |
| 5,514,470 A | 5/1996 | Haffner et al. |
| 5,527,302 A | 6/1996 | Endres et al. |
| 5,554,143 A | 9/1996 | Roe et al. |
| 5,554,144 A | 9/1996 | Roe et al. |
| 5,554,145 A | 9/1996 | Roe et al. |
| 5,556,394 A | 9/1996 | Roe et al. |
| 5,556,504 A | 9/1996 | Rajala et al. |
| 5,560,878 A | 10/1996 | Dragoo et al. |
| 5,569,232 A | 10/1996 | Roe et al. |
| 5,569,234 A | 10/1996 | Buell et al. |
| 5,582,903 A | 12/1996 | Levy et al. |
| 5,587,225 A | 12/1996 | Griesbach et al. |
| 5,611,790 A | 3/1997 | Osborn, III et al. |
| 5,615,460 A | 4/1997 | Weirich et al. |
| 5,624,422 A | 4/1997 | Allen |
| 5,624,427 A | 4/1997 | Bergman et al. |
| 5,624,729 A | 4/1997 | Cohen et al. |
| 5,628,741 A | 5/1997 | Buell et al. |
| 5,628,856 A | 5/1997 | Dobrin et al. |
| 5,635,290 A | 6/1997 | Stopper et al. |
| 5,643,396 A | 7/1997 | Rajala et al. |
| 5,645,542 A | 7/1997 | Anjur et al. |
| 5,645,672 A | 7/1997 | Dobrin |
| 5,658,269 A | 8/1997 | Osborn, III et al. |
| 5,660,657 A | 8/1997 | Rajala et al. |
| 5,674,212 A | 10/1997 | Osborn, III et al. |
| 5,683,375 A | 11/1997 | Osborn, III et al. |
| 5,690,627 A | 11/1997 | Clear et al. |
| 5,702,382 A | 12/1997 | Osborn, III et al. |
| 5,713,884 A | 2/1998 | Osborn, III et al. |
| 5,716,478 A | 2/1998 | Boothe et al. |
| 5,749,866 A | 5/1998 | Roe et al. |
| 5,749,989 A | 5/1998 | Linman et al. |
| 5,759,340 A | 6/1998 | Boothe et al. |
| 5,843,056 A | 12/1998 | Good et al. |
| 5,883,028 A | 3/1999 | Morman et al. |
| 5,910,224 A | 6/1999 | Morman |
| 5,928,211 A | 7/1999 | Gustafsson et al. |
| 6,004,306 A | 12/1999 | Robles et al. |

FOREIGN PATENT DOCUMENTS

| | | | |
|---|---|---|---|
| EP | 0 630 630 | 12/1994 | |
| EP | 0 630 631 | 12/1994 | |
| EP | 0 630 632 | 12/1994 | |
| EP | 0 420 256 | 5/1995 | |
| EP | 0 650 714 A1 | 5/1995 | |
| EP | 0 707 106 | 4/1996 | |
| EP | 0 433 951 | 8/1996 | |
| EP | 0 552 345 | 9/1996 | |
| EP | 0 630 221 | 4/1997 | |
| EP | 0 409 315 | 5/1997 | |
| EP | 0 820 747 | 1/1998 | |
| EP | 0 602 613 | 6/1998 | |
| EP | 0 651 629 | 6/1998 | |
| EP | 0 659 117 | 6/1998 | |
| EP | 1 064 895 A2 | 1/2001 | |
| WO | 93/01785 | 2/1993 | |
| WO | 93/17648 | 9/1993 | |
| WO | 94/02094 | 2/1994 | |
| WO | 96/16625 | 6/1996 | |
| WO | 96/18367 | 6/1996 | |
| WO | 97/36566 | 10/1997 | |
| WO | 98/37846 | 9/1998 | |
| WO | WO 9933424 A1 * | 7/1999 | ............ A61F/13/15 |
| WO | WO 9933426 A1 * | 7/1999 | ............ A61F/13/15 |
| WO | WO 01/15645 A1 | 3/2001 | |

* cited by examiner

ABSORBENT GARMENT WITH TRANSVERSE AND LONGITUDINAL STRETCH

FIELD OF THE INVENTION

This invention is directed to pant-like, personal care absorbent products that are stretchable in both a transverse direction and a longitudinal direction.

BACKGROUND OF THE INVENTION

Pant-like absorbent garments, such as adult incontinence wear as well as infant and children's diapers, swim wear and training pants, typically have some degree of stretchability in order to conform to a wearer's body. Present diapers, for example, have stretchable side panels with non-stretchable outer covers, body side liners and absorbent assemblies. When this type of diaper is worn, only the side panels stretch. The stretchable side panels provide a limited degree of stretchability in a transverse, or cross, direction.

A certain degree of stretchability in a longitudinal, or machine, direction is typically provided by leg elastics surrounding leg openings in the crotch region of an absorbent garment. However, this stretchability around the leg openings can undesirably result in a bulky, baggy area in the non-stretchable center of the crotch region. Furthermore, the movement of fecal matter is not restrained within the absorbent garment, hence fecal matter is free to move up the back of the absorbent garment, resulting in great discomfort to the wearer, in addition to a mess for a care giver to contend with.

There is a need or desire for a stretchable, form-fitting, pant-like, personal care absorbent garment that delivers an optimal amount and direction of stretch to provide optimal fit and comfort.

There is a further need or desire for a pant-like, personal care absorbent garment that restricts the movement of fecal matter within the garment.

SUMMARY OF THE INVENTION

The present invention is directed to a pant-like, personal care absorbent garment having three-piece construction to deliver machine and cross direction stretch in various regions of the garment. The garment provides enhanced fit and comfort during use, and ease of application with a self-adjusting feature.

The three-piece construction includes distinct front, back, and crotch panels. The front and back panels each stretch in a transverse, or cross, direction to provide a continuous waist force. The crotch panel stretches in a longitudinal, or machine, direction to provide adjustability of front panel positioning, ease of application, and self-adjusting fit after fastening. The stretchability in the longitudinal direction provides extra space for waste and provides additional length for movement and comfort without compromising overall fit.

The three separate panels may or may not be of the same materials. When the three separate panels are of the same material, the piece of material used as the crotch panel is rotated 90 degrees from the pieces of material used as the front and back panels. Seams joining the front and back panels to the crotch panel provide non-stretch zones that may be positioned to control fit forces. The non-stretch zone provided by the seam joining the back panel and the crotch panel can provide a force band to prevent fecal matter from moving up the back of the garment. The non-stretch zone provided by the seam joining the front panel and the crotch panel allows expansion of the abdominal region without affecting the fit below the abdomen, thereby maintaining front waist positioning.

In order to enable the garment's ability to stretch in the transverse and longitudinal directions, the remaining garment components must be able to expand in the corresponding directions. The three-piece construction can be applied to either the outer cover or the body side liner or both the outer cover and the body side liner. Extensibility of an absorbent layer can be accomplished in a number of different ways, including the use of elastic components, attaching absorbent material to a pre-stretched elastomer and allowing retraction before assembly, pleating the absorbent material, or using sliding absorbent panels which may or may not overlap.

With the foregoing in mind, it is a feature and advantage of the invention to provide a form-fitting, pant-like, absorbent garment that delivers an optimal amount and direction of stretch to provide optimal fit and comfort.

It is another feature and advantage of the invention to provide a pant-like, absorbent garment that restricts the movement of fecal matter within the garment.

DEFINITIONS

Figure 1:
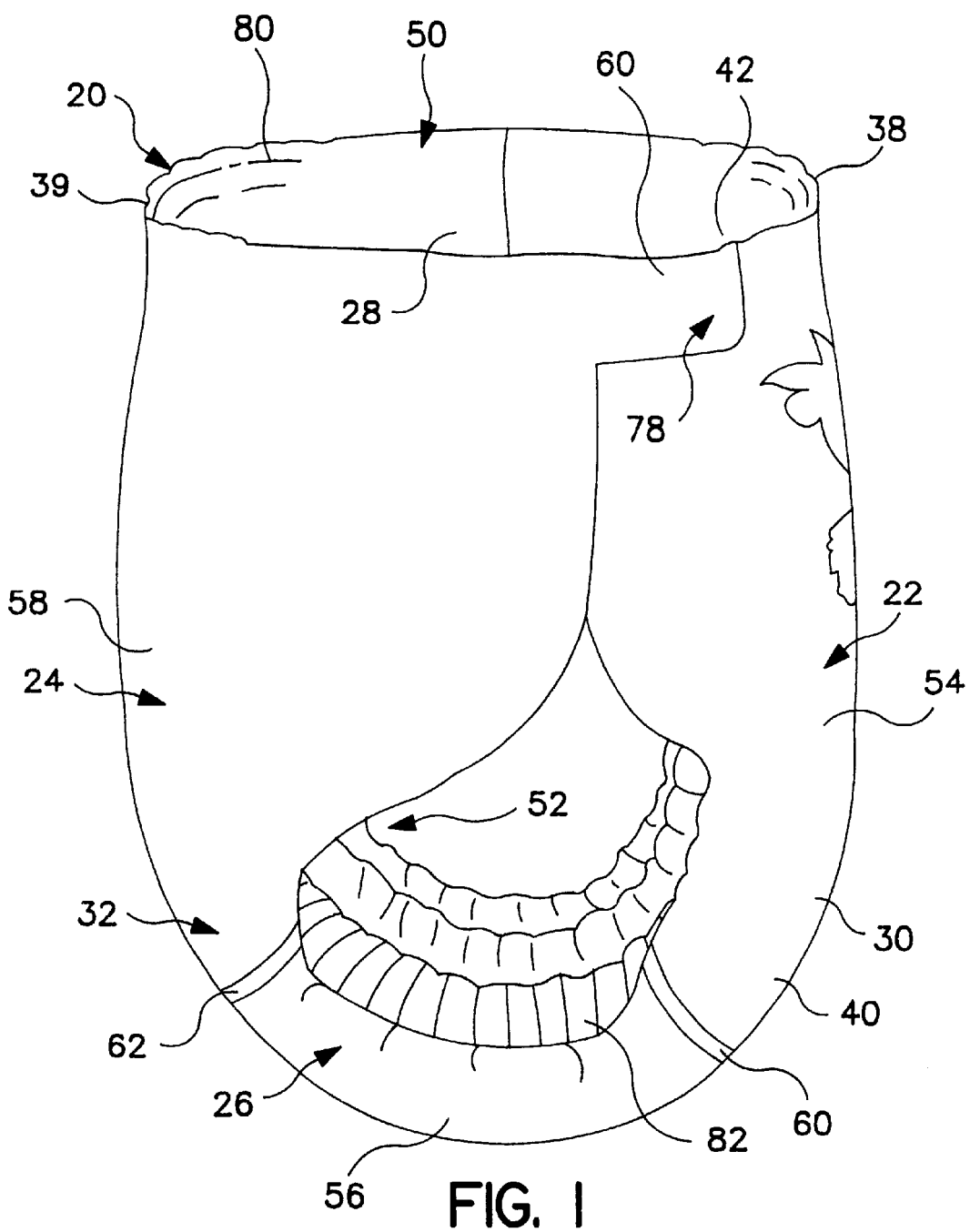
FIG. 1 is a side perspective view of an absorbent garment having a three-piece stretchable outer cover, in a fastened position.

Within the context of this specification, each term or phrase below will include the following meaning or meanings.

"Connected" refers to the joining, adhering, bonding, attaching, or the like, of two elements. Two elements will be considered to be connected together when they are connected directly to one another or indirectly to one another, such as when each is directly connected to intermediate elements.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material under normal use conditions.

Figure 2:
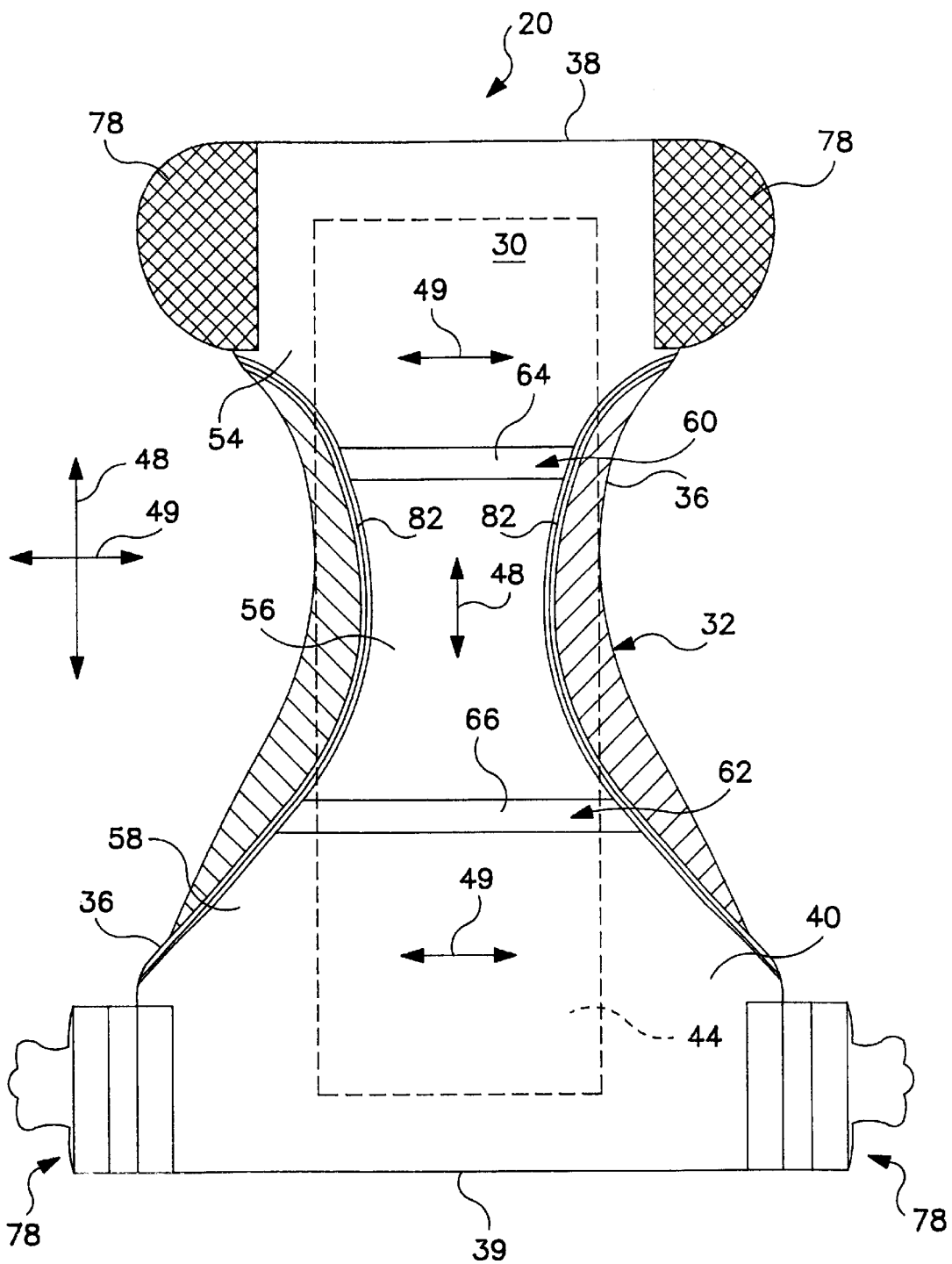
FIG. 2 is a plan view of the absorbent garment of FIG. 1 in a stretched flat state, and showing the surface of the article that faces away from the wearer when the article is worn.
Figure 3:
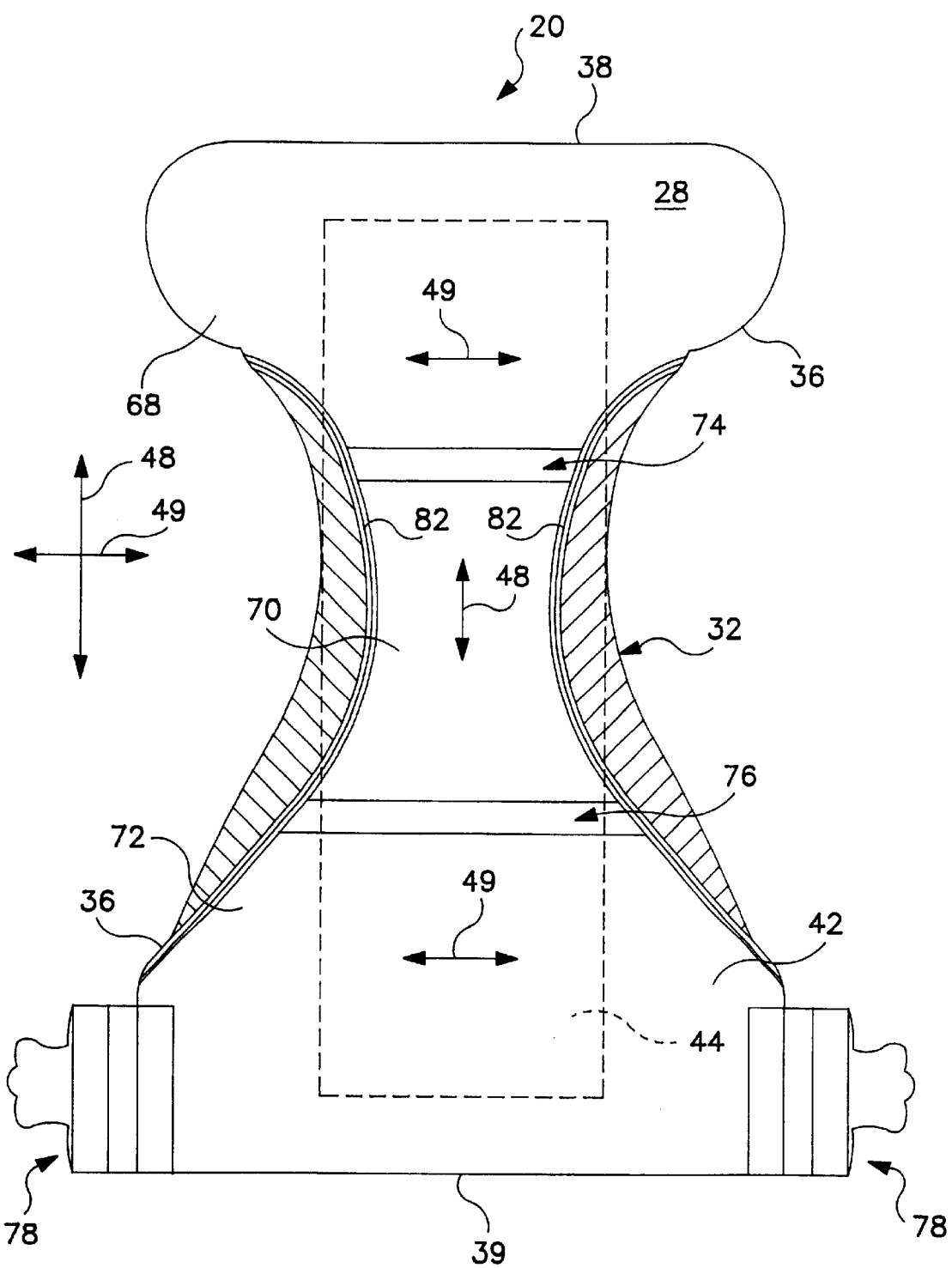
FIG. 3 is a plan view of the absorbent garment of FIGS. 1 and 2 in a stretched flat state, and showing the surface of the article that faces the wearer when the article is worn.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 decitex, and are generally self bonding when deposited onto a collecting surface. Meltblown fibers used in the present invention are preferably substantially continuous in length.

"Member" when used in the singular can have the dual meaning of a single element or a plurality of elements.

"Microfibers" are small diameter fibers typically having an average fiber denier of about 0.005–10. Fiber denier is defined as grams per 9000 meters of a fiber. For a fiber having circular cross-section, denier may be calculated as fiber diameter in microns squared, multiplied by the density in grams/cc, multiplied by 0.00707. For fibers made of the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 calculated as ($15^2 \times 0.89 \times 0.00707 = 1.415$). Outside the United States the unit of measurement is more commonly the "tex," which is defined as the grams per kilometer of fiber. Tex may be calculated as denier/9. A decitex is 0.1 of a tex.

"Necked" or "neck stretched" interchangeable refer to a method of elongating a nonwoven fabric, generally in the longitudinal, or machine direction, to reduce its width in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.4 times. When relaxes, the web retracts toward its original dimensions. Such a process is disclosed, for example, in U.S. Pat. Nos. 4,443,513 to Meitner and Notheis, 4,965,122, 4,981,747 and 5,114,781 to Morman and 5,244,482 to Hassenboehier Jr. et al.

"Nonwoven" and "nonwoven web" refer to materials and webs of material which are formed without the aid of a textile weaving or knitting process.

"Operatively attached," "operatively connected," and "operatively joined," in reference to the attachment of an elastic member to another element, mean that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Polymers" include, but are not limited to, homopolymers, copolymers, such as for example, block, graft, random and alternating copolymers, terpolymers, etc. and blends and modifications thereof. Furthermnore, unless otherwise specifically limited, the term "polymer" shall include all possible geometrical configurations of the material. These configurations include, but are not limited to isotactic, syndiotactic and atactic symmetries.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3 decitex, more particularly, between about 0.6 and 10 decitex.

"Stretchable" means that a material can be stretched, without breaking, to at least 150% of its initial (unstretched) length in at least one direction, suitably to at least 200% of its initial length, desirably to at least 250% of its initial length. The term includes elastic materials as well as materials that stretch but do not significantly retract.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a form-fitting, stretchable, pant-like, absorbent garment having a three-piece construction to enable longitudinal and transverse stretch in various regions.

The principles of the present invention can be incorporated into any suitable disposable, pant-like, absorbent article. Examples of such suitable articles include diapers, training pants, incontinence products, swim wear, other personal care or health care garments, or the like. For ease of explanation, the description hereafter will be in terms of a diaper.

Referring to FIGS. 1 and 2, a disposable absorbent article, such as a diaper 20, is illustrated. The diaper 20 includes an absorbent chassis 32. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. With additional reference to FIG. 2, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

As shown in the diaper 20 in FIG. 1, the crotch region 26, front and back regions 22 and 24 together define a three-dimensional pant configuration having a waist opening 50 and a pair of leg openings 52. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52. The front region 22 includes the portion of the diaper 20 which, when worn, is positioned on the front of the wearer while the back region 24 includes the portion of the diaper which, when worn, is positioned on the back of the wearer. The crotch region 26 of the diaper 20 includes the portion of the diaper which, when worn, is positioned between the legs of the wearer and covers the lower torso of the wearer.

The absorbent chassis 32 is configured to contain and/or absorb any body exudates discharged from the wearer. For example, the absorbent chassis 32 can include a pair of elasticized containment flaps (not shown) which are configured to provide a barrier to the transverse flow of body exudates. The elasticized containment flaps define an unattached edge which assumes an upright, generally perpendicular configuration in at least the crotch region 26 of the diaper 20 to form a seal against the wearer's body. Suitable constructions and arrangements for the containment flaps are generally well known to those skilled in the art and are described in U.S. Pat. No. 4,704,116 issued Nov. 3, 1987 to Enloe, which is incorporated herein by reference.

For reference, arrows 48 and 49 depicting the orientation of the longitudinal axis and the transverse axis, respectively, of the diaper 20 are illustrated in FIGS. 2 and 3.

The diaper 20 includes a stretchable outer cover 40, a stretchable body side liner 42 which is connected to the outer cover 40 in a superposed relation, and a stretchable absorbent assembly 44 which is located between the outer cover 40 and the body side liner 42, as shown in FIGS. 2 and 3.

FIG. 2 shows the stretchable outer cover 40 of the diaper 20. The outer cover 40 includes three separate panels: a front panel 54, a crotch panel 56 connected to the front panel 54, and a back panel 58 connected to the crotch panel 56. The front panel 54 and the back panel 58 can stretch in at least the transverse, or cross machine direction 49. The crotch panel 56 can stretch in at least the longitudinal, or machine direction 48.

The transverse stretch in the front and back panels 54, 58 provides a continuous waist force. The longitudinal stretch in the crotch panel 56 provides adjustability of front panel 54 positioning, ease of application, and self-adjusting fit after fastening. Also, the longitudinal stretch in the crotch panel 56 provides extra space for waste and provides additional length for movement and comfort without compromising overall fit.

In one embodiment, the front panel 54 and the back panel 58 can stretch only in the transverse direction 49, and the crotch panel 56 can only stretch in the longitudinal direction 48. In this embodiment, between the front panel 54 and the crotch panel 56, where the front panel 54 and the crotch panel 56 are joined together at a seam 64, a non-stretch zone 60 is formed. This non-stretch zone 60 is caused by the lack of transverse stretch of the crotch panel 56 hindering any transverse stretch in that zone 60, and further, by the lack of longitudinal stretch of the front panel 54 hindering any longitudinal stretch in that zone 60. This non-stretch zone 60 allows the front panel 54 to transversely expand along with a wearer's abdominal region without affecting the fit below the wearer's abdomen, thereby maintaining positioning of the front waist edge 38 of the diaper 20.

Also in this embodiment, another non-stretch zone 62 is formed between the back panel 58 and the crotch panel 56 where the back panel 58 and the crotch panel 56 are joined together at a seam 66. This non-stretch zone 62 is caused by the lack of transverse stretch of the crotch panel 56 hindering any transverse stretch in that zone 62, and further, by the lack of longitudinal stretch of the back panel 58 hindering any longitudinal stretch in that zone 62. This non-stretch zone 62 provides a force band to prevent fecal matter from moving up the back region 24 of the diaper 20.

The stretchable panels 54 and 58 of the outer cover 40 can suitably be stretched in the transverse direction 49 to at least 150% of an unstretched width of the panels 54 and 58. More suitably, the stretchable panels 54 and 58 of the outer cover 40 can be stretched in the transverse direction 49 to at least 200% of the unstretched width of the panels 54 and 58. Even more suitably, the stretchable panels 54 and 58 of the outer cover 40 can be stretched in the transverse direction 49 to at least 250% of the unstretched width of the panels 54 and 58. Similarly, the stretchable panel 56 of the outer cover 40 can suitably be stretched in the longitudinal direction 48 to at least 150% of an unstretched length of the panel 56. More suitably, the stretchable panel 56 of the outer cover 40 can be stretched in the longitudinal direction 48 to at least 200% of the unstretched length of the panel 56. Even more suitably, the stretchable panel 56 of the outer cover 40 can be stretched in the longitudinal direction 48 to at least 250% of the unstretched length of the panel 56.

The stretchable panels 54, 56, 58 of the outer cover 40 desirably include a material that is substantially liquid impermeable. The stretchable panels 54, 56, 58 can be a single layer of liquid impermeable material, but desirably include a multi-layered laminate structure in which at least one of the layers is liquid impermeable. For instance, the stretchable panels 54, 56, 58 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Ato-Findley Adhesives, Inc., of Wauwatosa, Wis., U.S.A., or from National Starch and Chemical Company, Bridgewater, N.J., U.S.A. Alternatively, rather than adhesive bonding, the outer layer and the inner layer can be joined together by ultrasonic bonding, thermal bonding, mechanical bonding, or any other suitable means.

The liquid permeable outer layer can be any suitable material and desirably one that provides a generally cloth-like texture. One example of such a material is a thermoplastic nonwoven web, such as a spunbond thermoplastic nonwoven web made from a stretchable polymer and having a basis weight of about 1–100 grams per square meter (gsm), suitably about 5–50 gsm, more suitably 10–30 gsm. Suitable stretchable polymers for making the nonwoven web include certain flexible polyolefins, for example propylene-based polymers having both atactic and isotactic propylene groups in the main polypropylene chain. Flexible polyolefins (FPO's) are sold by the Rexene Corporation. Also included are heterophasic propylene-ethylene copolymers sold as "catalloys" by the Himont Corporation. Heterophasic polymers are reactor blends formed by adding different levels of propylene and ethylene at different stages in the reactor. Heterophasic polymers typically include about 10–90% by weight of a first polymer segment A, about 10–90% by weight of a second polymer segment B, and 0–20% by weight of a third polymer segment C. Polymer segment A is at least about 80% crystalline and includes about 90–100% by weight propylene, as a homopolymer or random copolymer with up to 10% by weight ethylene. Polymer segment B is less than about 50% crystalline, and includes about 30–70% by weight propylene randomly copolymerized with about 30–70% by weight ethylene. Optional polymer segment C contains about 80–100% by weight ethylene and 0–20% of randomly copolymerized propylene.

Other stretchable polymers include very low density polyethylene (VLDPE), which is an ethylene-alpha olefin copolymer having a density less than 0.900 grams/cm$^3$, preferably about 0.870–0.890 grams/cm$^3$. Preferred VLDPE's are single-site catalyzed. Other stretchable polymers include random propylene-alpha olefin copolymers containing more than 10% by weight of a $C_2$ or $C_4$–$C_{12}$ comonomer, preferably about 15–85% by weight of the comonomer, with ethylene being a preferred comonomer.

The inner layer of the stretchable panels 54, 56, 58 of the outer cover 40 can be both liquid and vapor impermeable, or can be liquid impermeable and vapor permeable. The inner layer is desirably manufactured from a thin (1–50 microns, suitably 5–25 microns, more suitably 10–20 microns) plastic film, although other stretchable liquid impermeable materials may also be used. The film can contain a blend of a thermoplastic polymer and a 30–70% by weight of a particulate inorganic filler, such as calcium carbonate. The film can be oriented at least uniaxially to cause void formation around the filler particles, resulting in breathability. Suitable stretchable polymers for making the film include stretchable olefin polymers, such as an olefinic copolymer of polyethylene. More specifically, other stretchable polymers include diblock, triblock, tetrablock or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E. I. Du Pont de Nemours Co., under the trade name LYCRA® polyurethane; polyamides, including polyether block amides available from Ato-Findley Adhesives, Inc., under the trade name PEBAX® polyether block amide; polyesters, such as those available from E. I. Du Pont de Nemours Co., under the trade name HYTREL® polyester; and single-site or metallocene-catalyzed polyolefins having density less than about 0.89 grams/cc, available from Dow Chemical Co. under the trade name AFFINITY®. The inner layer, or the liquid impermeable stretchable outer cover 40 when a single layer, prevents waste material from wetting articles, such as bedsheets and clothing, as well as the wearer and care giver.

Suitable materials for the stretchable panels 54, 56, 58 of the outer cover 40 include stretch-bonded laminates (SBL) and neck-bonded laminates (NBL) made using a stretchable polymer or blend thereof. Techniques for neck-bonding, i.e., laminating a neckable nonwoven web to an unstretched elastic film or other layer of material, are described in U.S. Pat. No. 5,883,028, issued to Morman et al., which is incorporated by reference. The neckable nonwoven web may be a porous nonwoven material such as, for example, spunbonded web, meltblown web or bonded carded web. If the neckable material is a web of meltblown fibers, it may include meltblown microfibers. The neckable material may be made of fiber forming polymers such as, for example, polyolefins. Exemplary polyolefins include one or more of polypropylene, polyethylene, ethylene copolymers, propylene copolymers, and butene copolymers. Useful polypropylenes include, for example, polypropylene available from the Exxon Chemical Company under the trade designation Exxon 3445, and polypropylene available from Shell Chemical Company under the trade designation DX 5A09.

The neckable web may be a multilayer material having, for example, at least one layer of spunbonded web joined to at least one layer of meltblown web, bonded carded web or other suitable material. For example, neckable material may be a multilayer material having a first layer of spunbonded polypropylene having a basis weight from about 0.2 to about 8 ounces per square yard (osy) (about 6.8–270 grams/M$^2$, or gsm), a layer of meltblown polypropylene having a basis weight from about 0.2 to about 4 osy (6.8–135 gsm), and a second layer of spunbonded polypropylene having a basis weight of about 0.2 to about 8 osy (6.8–270 gsm). Alternatively, the neckable web may be a single layer of material such as, for example, a spunbonded web having a basis weight of from about 0.2 to about 10 osy (6.8–340 gsm) or a meltblown web having a basis weight of from about 0.2 to about 8 osy (6.8–270 gsm). The adjacent fibers of the web should be intermittently joined by interfiber bonding, using conventional techniques known in the art.

An elastic sheet may be joined to the neckable web when the latter is in the tensioned, necked state to form the neck-bonded laminate. The elastic sheet may be made from a water vapor permeable elastic polymer, or may be made from another elastic polymer and rendered vapor permeable by forming apertures or micropores in the sheet. Generally, the elastic film component of the neck-bonded laminate should be less than about 2 mils (50 micrometers) thick, preferably less than about 1 mil (25 micrometers) thick, more preferably less than about 0.5 mil (13 micrometers) thick, when the film and laminate are relaxed.

A more specific example of a suitable liquid impermeable film for use as a liquid impermeable inner layer, or a single layer liquid impermeable stretchable panel, is a 0.2 millimeter polyethylene film commercially available from Huntsman Packaging of Newport News, Va., U.S.A. If the stretchable panels are a single layer of material, they can be embossed and/or matte finished to provide a more cloth-like appearance. As earlier mentioned, the liquid impermeable material can permit vapors to escape from the interior of the disposable absorbent article, while still preventing liquids from passing through the stretchable panels of the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The panels 54, 56, 58 of the outer cover 40 are suitably one-way extendable, or one-way stretchable and retractable. Examples of materials having one-way stretchability and retractability are disclosed in U.S. Pat. No. 4,720,415 issued to Vander Wielen, et al., U.S. Pat. No. 5,336,545 issued to Morman, U.S. Pat. No. 4,981,747 issued to Morman, U.S. Pat. No. 5,226,992 issued to Morman, and U.S. Pat. No. 5,910,224 issued to Morman, all of which are hereby incorporated by reference.

The material used for the front and back panels 54, 48 of the outer cover 40 can be the same material used for the crotch panel 56 of the outer cover 40. When the material is stretchable in one direction only, the material can be rotated 90 degrees to provide stretch in the appropriate direction, i.e., transverse or longitudinal.

The body side liner 42 is illustrated in FIG. 3 as overlying the stretchable outer cover 40 and absorbent assembly 44, and may but need not have the same dimensions as the stretchable outer cover 40. The body side liner 42 needs to be stretchable in order to be able to expand along with the stretchable outer cover 40. Stretchable materials include those which are extensible and retractable as well as those that are extensible and non-retractable. The stretchable body side liner 42 is desirably compliant, soft feeling, and non-irritating to the child's skin. Further, the stretchable body side liner 42 can be less hydrophilic than the absorbent assembly 44, to present a relatively dry surface to the wearer and permit liquid to readily penetrate through its thickness.

The stretchable body side liner 42 can have the same type of three-piece construction as the outer cover 40, including a front panel 68, a crotch panel 70 attached to the front panel 68, and a back panel 72 attached to the crotch panel 70, but is made of a stretchable liner material rather than outer cover material. Similar to the panels 54, 56, 58 of the outer cover 40, the material used for the front and back panels 68, 72 of the body side liner 42 can be the same material used for the crotch panel 70 of the body side liner 42. When the material is stretchable in one direction only, the material can be rotated 90 degrees to provide stretch in the appropriate direction, i.e., transverse or longitudinal.

A non-stretch zone 74 between the front panel 68 and the crotch panel 70 serves to allow expansion of the wearer's abdominal region without affecting fit below the wearer's abdomen, just like the non-stretch zone 60 in the outer cover 40. Likewise, a non-stretch zone 76 between the back panel 72 and the crotch panel 70 of the body side liner 42 provides a force band to prevent fecal matter from moving up the back region 24 of the diaper 20, just like the non-stretch zone 62 in the outer cover 40. Either the outer cover 40 can have this three-piece construction, or the body side liner 42 can have this three-piece construction, or suitably both the outer cover 40 and the body side liner 42 can have this three-piece construction.

The stretchable body side liner 42 can be manufactured from a wide selection of web materials, such as synthetic fibers (for example, polyester or polypropylene fibers), a combination of synthetic and natural fibers (examples of natural fibers including cotton fibers), porous foams, reticulated foams, apertured plastic films, or the like. The stretchable body side liner 42 can suitably be composed of a neck-stretched spunbond web with Kraton® strands, or may composed of a reversibly necked, nonwoven web. Reversibly necked nonwovens are described in U.S. Pat. No. 4,965,122, issued to Morman, which is incorporated by reference.

The stretchable body side liner 42 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like. The surfactant can be applied to the entire stretchable body side liner 42 or can be selectively applied to particular sections of the stretchable body side liner, such as the medial section along the longitudinal centerline.

The absorbent assembly 44 (FIGS. 2 and 3) is positioned between the stretchable outer cover 40 and the stretchable body side liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent assembly 44 needs to be stretchable in order to be able to expand along with the stretchable outer cover 40 and the stretchable body side liner 42. The absorbent assembly 44 can be rendered stretchable by a number of different techniques, including the incorporation of elastic components, such as Kraton®, polypropylene co-form. Another technique includes attaching absorbent material, described above, to a pre-stretched elastomer and allowing the absorbent material and the elastomer to retract before assembling the absorbent assembly 44 within the diaper 20. Yet another technique includes pleating the absorbent material, and finally another technique includes using sliding absorbent panels which may or may not overlap one another.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 decitex type T-256 bicomponent fiber including a polyester core/polyethylene sheath and 40 percent 6 decitex type T-295 polyester fiber, both commercially available from Kosa Corporation of Salisbury, N.C., U.S.A.

The diaper 20 includes a fastening system 78 operatively attached to the outer cover 40 along the transversely opposed side edges 36 just below the waist edges 38 and 39. The fastening system 78 can include side panels with tabs, straps, tearable seams, or similar devices, that can be fastened to the front region 22 of the outer cover 40 by suitable means, including adhesives or hook and loop fasteners.

To further enhance containment and/or absorption of body exudates, the diaper 20 can include waist elastic members 80 and/or leg elastic members 82, as are known to those skilled in the art (FIG. 1). The waist elastic members 80 can be operatively joined to the stretchable outer cover 40 and/or the stretchable body side liner 42, and can extend over part or all of the waist edges 38, 39. The leg elastic members 82 are desirably operatively joined to the stretchable outer cover 40 and/or the stretchable body side liner 42 longitudinally along the opposite side edges 36 and positioned in the crotch region 26 of the diaper 20.

The waist elastic members 80 and the leg elastic members 82 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 82 include a plurality of dry-spun coalesced multifilament spandex elastomeric threads sold under the trade name LYCRA® and available from E.I. DuPont de Nemours and Company, Wilmington, Del., U.S.A.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent garment, comprising:
    a chassis having an outer cover, a body side liner, and an absorbent core between the outer cover and the body side liner, the chassis defining a waist opening and a pair of leg openings;
    the outer cover including a separate stretchable back panel, a separate stretchable crotch panel operatively connected to the stretchable back panel, and a separate stretchable front panel operatively connected to the stretchable crotch panel;
    wherein the stretchable back panel and the stretchable front panel can stretch in a transverse direction, and the stretchable crotch panel can stretch in a longitudinal direction.

2. The absorbent garment of claim 1, further comprising a non-stretch zone along a seam between the front panel and the crotch panel.

3. The absorbent garment of claim 1, further comprising a non-stretch zone along a seam between the back panel and the crotch panel.

4. The absorbent garment of claim 1, wherein the body side liner is stretchable.

5. The absorbent garment of claim 1, wherein the body side liner comprises a neck-stretched spunbond laminate.

6. The absorbent garment of claim 1, wherein the absorbent core is stretchable.

7. The absorbent garment of claim 1, wherein the absorbent core comprises elastic components.

8. The absorbent garment of claim 1, wherein the absorbent core comprises an absorbent material attached to a pre-stretched elastomer.

9. The absorbent garment of claim 1, wherein the absorbent core comprises a pleated absorbent material.

10. The absorbent garment of claim 1, wherein the absorbent core comprises sliding absorbent panels.

11. The absorbent garment of claim 1, wherein the outer cover comprises a stretch-bonded laminate.

12. The absorbent garment of claim 1, wherein the outer cover comprises a neck-bonded laminate.

13. An absorbent garment, comprising:

a chassis having an outer cover, a body side liner, and an absorbent core between the outer cover and the body side liner, the chassis defining a waist opening and a pair of leg openings;

the outer cover including a separate stretchable front panel, a separate stretchable crotch panel operatively connected to the stretchable front panel, a first non-stretch zone between the stretchable crotch panel and the stretchable front panel, a separate stretchable back panel operatively connected to the stretchable crotch panel, and a second non-stretch zone between the stretchable crotch panel and the stretchable back panel.

14. The absorbent garment of claim 13, wherein the stretchable back panel and the stretchable front panel can stretch in a transverse direction, and the stretchable crotch panel can stretch in a longitudinal direction.

15. The absorbent garment of claim 13, wherein the back panel and the front panel can be stretched transversely to at least 150% of an unstretched width of the back panel and the front panel.

16. The absorbent garment of claim 13, wherein the back panel and the front panel can be stretched transversely to at least 200% of an unstretched width of the back panel and the front panel.

17. The absorbent garment of claim 13, wherein the back panel and the front panel can be stretched transversely to at least 250% of an unstretched width of the back panel and the front panel.

18. The absorbent garment of claim 13, wherein the crotch panel can be stretched longitudinally to at least 150% of an unstretched length of the crotch panel.

19. The absorbent garment of claim 13, wherein the crotch panel can be stretched longitudinally to at least 200% of an unstretched length of the crotch panel.

20. The absorbent garment of claim 13, wherein the crotch panel can be stretched longitudinally to at least 250% of an unstretched length of the crotch panel.

21. The absorbent garment of claim 13, wherein the body side liner is stretchable.

22. The absorbent garment of claim 13, wherein the absorbent core is stretchable.

23. An absorbent garment, comprising:

a chassis having an outer cover, a body side liner, and an absorbent core between the outer cover and the body side liner, the chassis defining a waist opening and a pair of leg openings;

the outer cover and the body side liner each including a separate stretchable back panel, a separate stretchable crotch panel operatively connected to the stretchable back panel, and a separate stretchable front panel operatively connected to the stretchable crotch panel;

wherein the stretchable back panels and the stretchable front panels can stretch in a transverse direction, and the stretchable crotch panels can stretch in a longitudinal direction.

24. The absorbent garment of claim 23, further comprising a non-stretch zone along a seam between the front panel and the crotch panel of the outer cover.

25. The absorbent garment of claim 23, further comprising a non-stretch zone along a seam between the back panel and the crotch panel of the outer cover.

26. The absorbent garment of claim 23, further comprising a non-stretch zone along a seam between the front panel and the crotch panel of the body side liner.

27. The absorbent garment of claim 23, further comprising a non-stretch zone along a seam between the back panel and the crotch panel of the body side liner.

28. The absorbent garment of claim 23, comprising a diaper.

29. The absorbent garment of claim 23, comprising swim wear.

30. The absorbent garment of claim 23, comprising child training pants.

31. The absorbent garment of claim 23, comprising an adult incontinence garment.

* * * * *